United States Patent [19]
MacPhee et al.

[11] Patent Number: 5,981,252
[45] Date of Patent: Nov. 9, 1999

[54] LIPOPROTEIN ASSOCIATED PHOSPHOLIPASE A₂, INHIBITORS THEREOF AND USE OF THE SAME IN DIAGNOSIS AND THERAPY

[75] Inventors: Colin Houston MacPhee, Letchworth; David Graham Tew, Groby, both of United Kingdom

[73] Assignee: SmithKline Beecham, King of Prussia, Pa.

[21] Appl. No.: 08/387,858

[22] PCT Filed: Jun. 24, 1994

[86] PCT No.: PCT/GB94/01374

§ 371 Date: Feb. 24, 1995

§ 102(e) Date: Feb. 24, 1995

[87] PCT Pub. No.: WO95/00649

PCT Pub. Date: Jan. 5, 1995

[30] Foreign Application Priority Data

Jun. 25, 1993 [GB] United Kingdom .................. 9313144
Jan. 11, 1994 [GB] United Kingdom .................. 9400413

[51] Int. Cl.⁶ .............................. C12N 9/20; C07H 21/04
[52] U.S. Cl. .......................................... 435/198; 536/23.2
[58] Field of Search .............................. 435/198; 536/23.2

[56] References Cited

U.S. PATENT DOCUMENTS 5,532,152  7/1996  Cousens et al. .................. 435/197
5,641,669  6/1997  Cousens et al. .................. 435/195

FOREIGN PATENT DOCUMENTS 0 359 425 A1  8/1988  European Pat. Off. .
0 509 719 A1  10/1992  European Pat. Off. .
WO89/09818  10/1989  WIPO .

OTHER PUBLICATIONS

U.T. Kim, et al., "Synthesis of Phospholipid Headgroups via Nucleophilic Ring Opening of 1.3.2–Dioxaphospholanes", *J. Chem. Soc., Chem. Commun.*, pp. 70–71 (1993).

N. S. Chandrakumar. et al., "Stereospecific Synthesis of Ehter Phospholipids. Preparation of 1–Alkyl–2–(acylamino)–2–deoxyglycerophosphorylcholines", *J. Org. Chem*, pp. 1197–1202 (1983).

M.M. Ponpipom, et al., "Synthesis of Azide and Amide Analogs of Platelet–Activating Factor and Related Derivatives", *Chem. Phys. Lipids*, 35, pp. 29–37 (1984).

Langlais, J. et al. (1991) *Biology of Reprod.* 44(Suppl. 1): p. 94, abstract 166.

Stafforini, D.M. et al. (1987) "Human plasma platetlet–activating factor acetylhydrolase " J. Biol. Chem. 262(9):4223–4230, Mar. 1987.

Stafforini, D.M. et al. (1990) "Human macrophages secrete platelet–activating factor acetylhydrolase" J. Biol. Chem. 265(17):9682–9687, Jun. 1990.

*Primary Examiner*—Bradley L. Sisson
*Assistant Examiner*—Einar Stoce
*Attorney, Agent, or Firm*—Shanks & Herbert

[57] ABSTRACT

The enzyme Lp-PLA₂ in purified form, an isolated nucleic acid molecule encoding Lp-PLA₂, the use of an inhibitor of the enzyme Lp-PLA₂ in therapy and a method of screening compounds to identify those compounds which inhibit the enzyme.

5 Claims, 2 Drawing Sheets

LIPOPROTEIN ASSOCIATED PHOSPHOLIPASE A$_2$, INHIBITORS THEREOF AND USE OF THE SAME IN DIAGNOSIS AND THERAPY

The present invention relates to the use of inhibitors of an enzyme in the therapy, in particular in the treatment of atherosclerosis. The present invention also relates to the isolation and purification of the enzyme, to isolated nucleic acids encoding the enzyme, to recombinant host cells transformed with DNA encoding the enzyme, to the use of the enzyme in diagnosing a patient's susceptibility to atherosclerosis, and to the use of the enzyme in identifying compounds which are potentially useful for the treatment of atherosclerosis.

Lipoprotein Associated Phospholipase A$_2$ (Lp-PLA$_2$), also previously known in the art as Platelet Activating Factor Acetyl Hydrolase (PAF acetyl hydrolase). During the conversion of LDL to its oxidised form, Lp-PLA$_2$ is responsible for hydrolysing the sn-2 ester of oxidatively modified phosphatidylcholine to give lyso-phosphatidylcholine and an oxidatively modified fatty acid. Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis. Inhibition of the Lp-PLA$_2$ enzyme would therefore be expected to stop the build up of this fatty streak (by inhibition of the formation of lysophosphatidylcholine), and so be useful in the treatment of atherosclerosis. In addition, it is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process. In keeping with this idea, Lp-PLA$_2$ inhibitors inhibit LDL oxidation. Lp-PLA$_2$ inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction, reperfusion injury and acute and chronic inflammation.

The present invention therefore provides in a first aspect an inhibitor of the enzyme lipoprotein associated Lp-PLA$_2$ for use in therapy, in particular in the treatment of atherosclerosis. Suitable compounds able to inhibit the Lp-PLA$_2$ enzyme are known in the art and include for example, the following compounds of structure (I):

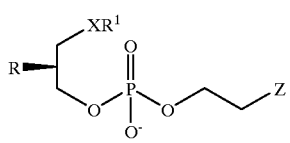

(I)

which R is C$_{1-6}$alkylCONR$^2$;

R$^2$ is hydrogen or C$_{1-6}$alkyl;

X is oxygen, sulphur or —O(CO)—;

R$^1$ is C$_{8-20}$alkyl;

Z is N(R$^3$)$_2$, $^{\oplus}$N(R$^3$)$_3$, SR$^3$, $^{\oplus}$S(R$^3$)$_2$, in which each group R$^3$ is the same or different and is C$_{1-6}$ alkyl, OR$^2$, C$_{1-4}$alkanoyl, imidazolyl or N-methylimidazolyl Suitably R$^2$ is hydrogen or C$_{1-6}$ alkyl; preferably R$^2$ is hydrogen.

Suitably X is oxygen, sulphur or —O(CO)—; preferably X is oxygen

Suitably R$^1$ is C$_{8-20}$alkyl; preferably R$^1$ is C$_{16-18}$ alkyl

Suitably Z is N(R$^3$)$_2$, $^{\oplus}$N(R$^3$)$_3$, SR$^3$, $^{\oplus}$S(R$^3$)$_2$, in which each group R$^3$ is the same or different and is C$_{1-6}$ alkyl, OR$^2$, C$_{1-4}$alkanoyl, imidazolyl or N-methylimidazolyl; preferably Z is SR$^3$ in which R$^3$ is methyl or OR$^2$ in which R$^2$ is hydrogen The compounds of structure (I) can be prepared by processes known to those skilled in the art, for example as described in J Chem Soc Chem Comm., 1993, 70–72; J Org Chem, 1983, 48, 1197 and Chem Phys Lipids, 1984,35, 29–37 or procedures analogous thereto.

When used in therapy, the compounds of structure (I) are formulated in accordance with standard pharmaceutical practice.

The compounds of structure (I) and their pharmaceutically acceptable salts which are active when given orally can be formulated as liquids, for example syrups, suspensions or emulsions, tablets, capsules and, lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy.

The enzyme, lipoprotein associated Lp-PLA$_2$ has not hitherto been available in isolated purified form. The present invention therefore provides in a further aspect, the enzyme lipoprotein associated Lp-PLA$_2$ in purified form. By purified form is meant at least 80%, more preferably 90%, still more preferably 95% and most preferably 99% pure with respect to other protein contaminants.

The enzyme Lp-PLA$_2$ may be characterised by one or more partial peptide sequences selected from SEQ ID NOs:1, 2, 3, 4, 10 and 11 or by the partial peptide sequence comprising residues 271 to 441 or consisting of residues 1 to 441 of SEQ ID NO:9. The enzyme Lp-PLA$_2$ may further or alternatively characterised by its molecular weight found to be 45 kDa, at least 45 kDa, 45–47 kDa, 46–47 kDa or 45–50 kDa.

The invention also provides fragments of the enzyme having Lp-PLA$_2$ activity.

The enzyme can be isolated and purified using the methods hereafter described. Once isolated, the protein sequence of the enzyme can be obtained using standard techniques. In identifying said sequence, a number of protein fragments have been identified, each of which comprises part of the whole sequence of the enzyme. These sequences are themselves novel and form a further aspect of the invention.

This invention also provides isolated nucleic acid molecules encoding the enzyme, including mRNAs, DNAs, cDNAs as well as antisense analogs thereof and biologically active and diagnostically or therapeutically useful fragments thereof.

In particular, the invention provides an isolated nucleic acid molecule consisting of bases 1 to 1361 or 38 to 1361 or comprising the sequence corresponding to bases 848 to 1361 of SEQ ID NO: 9.

This invention also provides recombinant vectors, such as cloning and expression plasmids useful as reagents in the recombinant production of the enzyme, as well as recombinant prokaryotic and/or eukaryotic host cells comprising the novel nucleic acid sequence.

This invention also provides nucleic acid probes comprising nucleic acid molecules of sufficient length to specifically hybridize to the novel nucleic acid sequences.

This invention also provides an antisense oligonucleotide having a sequence capable of binding with mRNAs encoding the enzyme so as to prevent the translation of said mRNA.

This invention also provides transgenic non-human animals comprising a nucleic acid molecule encoding the enzyme. Also provided are methods for use of said transgenic animals as models for mutation and SAR (structure/activity relationship) evaluation as well as in drug screens.

This invention further provides a method of screening compounds to identify those compounds which inhibit the enzyme comprising contacting isolated enzyme with a test compound and measuring the rate of turnover of an enzyme substrate as compared with the rate of turnover in the absence of test compound.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the sense strand of DNA.

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule and includes allelic variations. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience. Ausbel et al. (ed.) (1992). Protein sequences that are substantially the same can be identified by proteolytic digestion, gel electrophoresis and microsequencing.

The term "functionally equivalent" intends that the amino acid sequence of the subject protein is one that will exhibit enzymatic activity of the same kind as that of Lp-PLA$_2$.

A "heterologous" region of a DNA construct is an identifiable segment of DNA within or attached to another DNA molecule that is not found in association with the other molecule in nature.

This invention provides an isolated nucleic acid molecule encoding the enzyme Lp-PLA$_2$. One means for isolating the coding nucleic acid is to probe a human genomic or cDNA library with a natural or artificially designed probe using art recognized procedures (See for example: "Current Protocols in Molecular Biology", Ausubel, F. M., et al. (eds.) Greene Publishing Assoc. and John Wiley Interscience, New York, 1989, 1992); for example using the protein fragment information disclosed herein. The enzyme of this invention may be made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g. yeast, insect or mammalian) cells by methods well known in the art (Ausubel et al.,supra). The coding sequences for the desired proteins having been prepared or isolated, can be cloned into a suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, YCp19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The protein sequences of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site. Modification of the coding sequences may also be performed to alter codon usage to suit the chosen host cell, for enhanced expression.

In some cases, it may be desirable to add sequences which cause the secretion of the polypeptide from the host organism, with subsequent cleavage of the secretory signal. It may also be desirable to produce mutants or analogs of the enzyme of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1 (*Mol. Cell Biol.* 7:4125–29) which uses the CMV promoter to drive expression. Both these latter two vectors can be employed for transient or stable(using G418 resistance) expression in mammalian cells. Insect cell expression systems, e.g., *Drosophila*, are also useful, see for example, PCT applications U.S. Pat. No. 89/05155 and U.S. Pat. No. 91/06838 as well as EP application 88/304093.3.

Depending on the expression system and host selected, the enzyme of the present invention may be produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. Where the protein is localized to the cell surface, whole cells or isolated membranes can be used as an assayable source of the desired gene product Protein expressed bacterial hosts such as E. coli may require isolation from inclusion bodies and refolding. The selection of the appropriate growth conditions and recovery methods are within the skill of the art.

The identification of this novel target for the treatment of atherosclerosis, also leads to a novel diagnostic method to diagnose a patient's susceptibility to developing atherosclerotic disease.

The present invention therefore provides in a still further aspect a diagnostic method comprising isolating a sample of blood from the patient, and assaying said sample for Lp-PLA$_2$ activity. Patients that are susceptible to atherosclerotic disease are expected to have elevated levels of the Lp-PLA$_2$ enzyme, and hence the levels of Lp-PLA$_2$ provides an indication of the patient's susceptibility to atherosclerotic disease. Moreover, Lp-PLA$_2$ is found located predominantly on dense subfraction(s) of LDL which are known to be very atherogenic. Plasma Lp-PLA$_2$ levels could therefore provide a ready measure of these very atherogenic small dense LDL particles.

It is expected that the presence of the enzyme in the blood sample of the patient can be assayed by analysis of enzyme activity (i.e. by an assay set up against the purified enzyme as standard); or alternatively by assaying protein content of the sample by using polyclonal or monoclonal antibodies prepared against the purified enzyme. Monoclonal (and polyclonal) antibodies raised against the purified enzyme or fragments thereof are themselves novel and form a further aspect of the invention.

DATA AND EXAMPLES

1. Screen for Lp-PLA$_2$ Inhibition.

Enzyme activity was determined by measuring the rate of turnover of the artificial substrate (A) at 37° C. in 50 mM HEPES (N-2-hydroxyethylpiperazine-N'-2-ethanesulphonic acid) buffer containing 150 mM NaCl, pH 7.4.

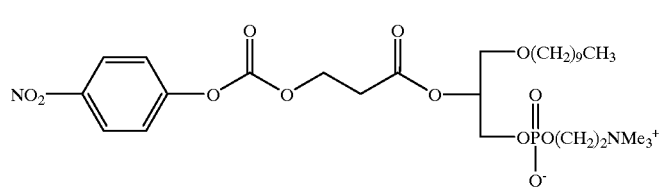

(A)

Assays were performed in 96 well titre plates.

Lp-PLA$_2$ was pre-incubated at 37° C. with vehicle or test compound for 10 min in a total volume of 180 μL. The reaction was then initiated by the addition of 20 μl 10× substrate (A) to give a final substrate concentration of 20 μM. The reaction was followed at 405 nm for 20 minutes using a plate reader with automatic mixing. The rate of reaction was measured as the rate of change of absorbance.

RESULTS

| Compound No | XR$^1$ | R | Z | IC$_{50}$ (μM) |
|---|---|---|---|---|
| 1 | O(CH$_2$)$_{15}$CH$_3$ | CH$_3$CONH | N$^+$(CH$_3$)$_3$ | 0.8 |
| 2 | O(CH$_2$)$_{17}$CH$_3$ | CH$_3$CONH | N$^+$(CH$_3$)$_3$ | 3.5 |
| 3 | O(CH$_2$)$_{17}$CH$_3$ | CH$_3$CONH | S$^+$(CH$_3$)$_2$ | 1.0 |
| 4 | O(CH$_2$)$_{17}$CH$_3$ | CH$_3$CONH | SCH$_3$ | 0.08 |

-continued

| Compound No | XR$^1$ | R | Z | IC$_{50}$ (μM) |
|---|---|---|---|---|
| 5 | O(CH$_2$)$_{17}$CH$_3$ | CH$_3$CONH | OH | 0.45 |
| 6 | O(CH$_2$)$_{17}$CH$_3$ | CH$_3$CONH | OAc | 0.2 |
| 7 | O(CH$_2$)$_{17}$CH$_3$ | CH$_3$CONH | imidazole | 0.5 |
| 8 | O(CH$_2$)$_{17}$CH$_3$ | CH$_3$CONH | N-methylimidazolium | 0.55 |
| 9 | O(CH$_2$)$_{17}$CH$_3$ | CF$_3$CONH | N$^+$(CH$_3$)$_3$ | 2.5 |

2. Copper Stimulated LDL Oxidation:

Copper stimulated oxidation of LDL is routinely measured by following the increase in conjugated diene formation by monitoring the change in absorption at 234 nm. This assay can be used to study inhibitors of oxidative modification of LDL. FIG. 1 demonstrates that Lp-PLA$_2$ inhibitors are effective inhibitors of LDL oxidation through a prolongation of the lag phase, using compound 4 as an example.

3. Inhibition of Cu$^{2+}$ stimulated lyso-phosphatidylcholine (lyso-PtdCho) formation.

A 1 ml aliquot of human LDL (0.25 mg protein/ml) was incubated for 15 min at 37° C. with compound or vehicle. 5 μM Cu$^{2+}$ was then added to allow oxidation/lyso-PtdCho formation to occur. The incubation was terminated by the addition of 3.75 ml chloroform/methanol/c HCl (200:400:5, v/v/v). Following the addition of 1.25 ml chloroform and 1.25 ml 0.1M HCl, the mixture was vortexed and centrifuged. The lower phase was carefully removed and the upper phase re-extracted with an equal volume of synthetic lower phase. The extracts were pooled and dried under nitrogen.

Phospholipids were reconstituted into 50 μl chloroform/methanol (2:1 v/v). 10 μl aliquots were spotted on to pre-run silica gel HPTLC plates and then developed in chloroform/methanol 25–30% methylamine (60:20:5 v/v/v). Plates were subsequently sprayed with the flourescent indicator, 2-p-toluidinylnaphthalene-6-sulphonic acid (1 mM in 50 mM Tris/HCl, pH 7.4) to identify phospholipid components. Fluorescence was measured at 222 nm using a CAMAG TLC scanner. Lipoprotein lyso-PtdCho content was quantified using a standard curve (0.05–0.5 μg) prepared in parallel.

Compound 4 dose dependently inhibits LDL lyso-PtdCho accumulation stimulated by copper ions with an IC$_{50}$ value of ~30 μM.

4. Purification of Lipoprotein Associated Lp-PLA$_2$

Low density lipoprotein (LDL) was obtained by plasma apheresis. The LDL was dialysed against 0.5 M NaCl, 50 mM MES (4-morpholine ethane sulphonic acid), pH=6.0 overnight at 4° C. Solid CHAPS (3-[(-3-cholamidopropyl)

dimethylamino]-1-propane sulphonate) was added to 10 mM and the LDL stirred for 30 minutes to effect solubilisation. The solubilised LDL was pumped onto a pre-equilibrated Blue Sepharose 6FF (Pharmacia) column (2.6× 20 cm). The column was then washed with 50 mM MES, 10 mM CHAPS, 0.5 M NaCl, pH=6.0 followed by 50 mM Tris, 10 mM CHAPS, 0.5 M NaCl, pH=8.0 until the absorbance (280 nm) of the eluate reached zero. Lp-PLA$_2$ was eluted using 50 mM Tris, 10 mM CHAPS, 1.5 M NaCl, pH=8.0. The Lp-PLA$_2$ fraction was then concentrated and dialysed overnight against 50 mM Tris, 10 mM CHAPS, pH=8.0.

The dialysed Lp-PLA$_2$ was submitted to anion exchange chromatography on a mono Q column (Pharmacia) using 50 mM Tris, 10 mM CHAPS, pH=8.0 with a NaCl gradient from zero to 0.3 M. The Lp-PLA$_2$ fractions obtained from the mono Q column were applied directly to a Hi Trap Blue cartridge (Pharmacia). The cartridge was washed with 50 mM Tris, 10 mM CHAPS, 0.5 M NaCl, pH=8.0 until the absorbance of the eluate (280 nm) was zero. Lp-PLA$_2$ was then eluted using 50 mM Tris, 10 mM CHAPS, 1.5 M NaCl, pH=8.0. This gave Lp-PLA$_2$ which is greater than 95% pure as shown in FIG. 2. This also demonstrates that the native enzyme is extensively glycosylated.

5. Enzyme Sequence

The purity of the final enzyme preparation was verified by five criteria 1) SDS-polyacrylamide gel electrophoresis gave one band for both native and deglycosylated forms. 2) Reverse phase high pressure liquid chromatography (RP-HPLC) gave a single peak, 3) The intact preparation gave no results by protein sequencing, implying that the protein was N-terminally blocked and free of any contaminants with open N-terminals, 4) By laser desorbtion mass spectometry only one broad peak was observed with de-glycosylated protein, and 5) none of the sections of extended peptide data from sequencing gave any databse matches indicative of contaminating proteins. Three cleavage strategies were used to obtain internal sequence information; trypsin (after de-glycosylation), cyanogen bromide (methionine cleavage) and BNPS-Skatol (tryptophan cleavage). The resulting peptides were separated by RP-HPLC, collected and sequenced. The accumulated sequence data allowed several extended stretches of primary structure of the Lp-PLA2 enzyme to be verified. These are shown below as Peptides 1, 2, 3 and 4 (SEQ ID Nos 1 to 4). When searched against the National Centre for Biotechnological information (NCBI) non-redundant peptide sequence databases no high similarity matches were obtained. Estimation of the molecular weight of pure, de-glycosylated protein by laser desorption mass spectrometry gives values in the region of 45–47 kDa (separately 45 kDa and 46–47 kDa), indicating that the sequences constitute approximately 15 to 20% of the protein.

6. Gene Sequence

Three expressed sequence tags (ESTs) from human cDNA libraries have been found to have extensive alignments with the Peptide Sequences 1 to 3. These EST's are shown below as Nucleotide Sequences 1 to 3 (SEQ ID Nos: 5 to 7) Nucleotide Sequence 1 is a 420 base sequence derived from a human foetal spleen library. Nucleotide Sequence 2 is a 379 base sequence derived from a 12-week human embryo library. Nucleotide Sequence 3 is a 279 base sequence derived from a T-cell lymphoma library. The identities at both the nucleic acid and amino acid level justified an overlapping alignment of the cDNA of all three ESTs, Nucleotide Sequences 3 (bases 1-278), 1 (bases 1-389) (in reverse orientation) and 2 (bases 1-304) with the Peptide Sequences 1, 2 and 3 (partially). Beyond these limits, the poor resolution of the raw sequence data precludes accurate base calling.

There are two remaining unassigned peptide sections from Peptides 3 and 4, both of which are expected to be present in the complete protein, -Q-Y-I-N-P-A-V-, and W-L-M-G-N-I-L-R-L-L-F-G-S-M-T-T-P-A-N-. (SEQ ID Nos: 3 and 4, respectively.)

7. Isolation of Full-length Lp-PLA$_2$ cDNA

The full DNA sequence was determined for the clone (HLTA145) from which the Lymphoma EST (SEQ ID No:7) was derived, giving a total of 572 bases; SEQ ID No:8. There is one base difference between this sequence and the EST (between bases 1 to 256 of the EST); at position 27 of HLTA145 there is an A compared with a T in the EST. This would cause a coding change; L in HLTA145 compared with F in the EST. Clone HLTA145 was used as a radiolabelled probe to screen the Lymphoma cDNA library in order to isolate the full-length Lp-PLA$_2$ clone. The library was prepared in the bacteriophage λ vector, Unizap XR (Stratagene).

Preparation of the Filters for Screening

The library was plated out at a density of 20,000 plaques per 150 mm petri dish onto E.coli XL-1 Blue host cells (ie. 200,000 plaques on 10 dishes). An overnight of XL-1 Blue was prepared in 100 mls LB/0.2% w/v Maltose/10 mM MgSO$_4$. The cells were pelleted, resuspended in 50 mls 10 mM MgSO$_4$ and stored on ice. 180 µl of the library bacteriophage stock (23,400 pfu's) were added to 7 mls XL-1 Blue cells, mixed and divided into 10 aliqouts of 615 µl. The 10 tubes were incubated at 37° C. for 30 minutes. 7 mls of molten (@45° C.) top agarose (0.7% w/v agarose in LB) were added, mixed well and poured onto 150 mm LB agar plates (1.5% w/v agar in LB). The plates were inverted and incubated at 37° C. for approximately 7.5 hours. The plates were held at 4° C. until needed.

The plaques were transfered to 132 mm Hybond-N nylon filters (Amersham International) by laying the filters on the plates for 2 minutes (4 minutes for the duplicate). The DNA's on the filters were denatured for 2 minutes (0.5M NaCl, 15M NaOH), neutralised for 4 minutes (1.5M NaCl, 1.0M Tris pH7.4) and the filters placed on 2× SSC for 1 minute. The filters were then dried and the DNA cross-linked to the filter using a Stratalinker UV 2400 (Stratagene) at 120,000 µJuoles/cm$^2$.

The filters were pre-hybridised in 1 mM EDTA, 0.5M NaHPO$_4$, 7% SDS (Church, G M. and Gilbert, W. (1984) PNAS USA 81 p1991–1995) in a Techne HB2 hybridisation oven at 55° C. for 3 hours. Each bottle contained 2 filters and 25 mls prehybridization solution.

Preparation of the Radiolabelled Probe

The probe cDNA (from HLTA 145) was excised from pBluescript II SK+/− as an approximately 600 bp EcoRI-XhoI fragment and approximately 100 ng of gel purified fragment were labelled using 1.2 MBq $^{32}$P dATP and 1.2 MBq $^{32}$P dCTP by PCR labelling using Taq DNA polymerase (Boehringer Mannheim) and primers designed to prime at the 5' and 3' ends of the EST sequence. The labelling reaction was carried out in a total volume of 200 µl and included unlabelled dNTP's at the following concentrations:

dATP 20 µM
dCTP 20 µM
dGTP 200 µM
dTTP 200 µM

The PCR reaction was carried out over 35 cycles of:
94° C. for 30s
60° C. for 30s
72° C. for 30s Screening The radiolabelled probe was denatured at 98° C. for 5 minutes and divided into 10 aliquots of 20 μl. One aliquot was added per hybridisation bottle. Hybridisation was carried out over 16 hours at 55° C. The filters were washed at 60° C. (2×10 minutes) with 0.1% w/v SDS, 0.1× SSC (50 mls per wash per bottle). The filters were autoradiographed and the films (Fuji Medical X-Ray Film) developed after 5 days exposure.

Duplicate positives were progressed to a secondary screen. The plaques were cored out into 1 ml SM (100 mM NaCl, 10 mM $MgSO_4$, 1M Tris, pH7.4), titrated and plated onto 90 mm petri dishes at between 20 and 200 pfu's per dish. The secondary screen was carried out as described for the primary screen except the filters were washed at 65° C. The autoradiographs were developed after 16 hours exposure.

DNA Sequencing

The duplicated positive clones from the secondary screen were excised from the λ Unizap XR bacteriophage vector into the Bluescript phagemid (according to the Stratagene manual) for characterisation. One of the clones, carrying an insert of approximately 1.5 kb, was sequenced on both strands (using the USB Sequenase 2.0 DNA sequencing kit) by primer walking (SEQ ID No:9). The cDNA has an open reading frame with the potential to code for a polypeptide of 441 amino acids.

The 3' region of the full-length cDNA aligns with the HLTA145 sequence with the exception of 3 mismatches (see below). The predicted polypeptide sequence of the lymphoma $Lp-PLA_2$ is shown as SEQ ID No:9.

Inspection of the full length cDNA (SEQ ID No: 9) reveals probable errors in Peptide 3. One of these errors is in the assignment of continuity between V-M which is incompatible with the perfect sequence match with the cDNA after this position. It seems likely that a short peptide, containing the sequence -Q-Y-I-N-P-, co-purified with the longer cyanogen bromide partial cleavage peptide and, by being present in greater quantity, was assigned as the major sequence and contiguous with the subsequent amino acids. The remaining section of Peptide 3 and the whole of Peptide 4 can be identified in the predicted full length enzyme sequence (SEQ ID No:9). It thus seems likely that Peptide 3 is in fact two separate Peptides 5 (SEQ ID No: 10) and 6 (SEQ ID No: 11). The second probable error has occurred in the transcription from the raw data for Peptide 3 which on checking was consistent with Peptide 5 having the sequence -Q-Y-I-N-P-V-A, rather than Q-Y-I-N-P-A-V-.

The 3 base differences are as follows:

1) T at 859 is A in HLTA145; aminoacid change F in full-length, L in HLTA145. (Note that the original EST is identical with the full-length cDNA at position 859).
2) C at 1173 is T in HLTA145; aminoacid change A in full-length, V in HLTA145.
3) T at 1203 is C in HLTA145; aminoacid change L in full-length, S in HLTA145.

The peptide data and the Foetal Spleen EST sequence (SEQ ID No:5) support the full-length cDNA sequence for differences (2) and (3) although the Human Embryo EST (SEQ ID No:6) is identical to the Lymphoma EST (SEQ ID No:7) at position 1173. The Human Embryo EST (SEQ ID No:6) has a further difference (4) corresponding to position 1245 in the full-length Lymphoma sequence (SEQ ID No:9) (comparison between bases 2 to 304 of the Human Embryo EST and the full-length Lymphoma cDNA).

4) A at 1245 is T in the Embryo EST (SEQ ID No:6) (amino acid change D to V in the Embryo EST).

Peptide data covering this region supports the Lymphoma DNA sequence (SEQ ID No:9).

The $Lp-PLA_2$ DNA sequence from 848 to 1361 of SEQ ID No:9 (amino acid residues 271 to 441 of SEQ ID No:9) is the region for which all major data sets agree substantially, ie. the peptide data, the Foetal spleen, full-length Lymphoma and it includes the known active site and is therefore believed to be a significant characterising region for the $Lp-PLA_2$ enzyme.

The predicted MW for the full reading frame is 50090. This in in exess of that determined for the de-glycosylated, purified protein but post-translational events could account for this discrepancy. The most likely of these are the removal of an N-terminal signal peptide and/or limited proteolytic degradation of the protein C-terminal. The latter could occur in-vivo, during purification, or under the conditions of de-glycosylation.

DIAGNOSTIC METHOD

A sample of blood is taken from a patient, the plasma/serum sample prepared and passed through a dextran sulphate column pre-equilibrated with 0.9% (w\v) NaCl solution. Following washes with the same salt solution $Lp-PLA_2$ is eluted with a 4.1% (w\v) NaCl solution. Heparin agarose columns can also be used with the wash and elution solutions containing 0.7% and 2.9% NaCl, respectively. Enzyme present in the sample is determined by assaying for either (a) Enzyme Activity:

The substrate (A) (see structure in 1) is used to assay $Lp-PLA_2$ activity by monitoring the absorbance change at 400 nm. Purified enzyme is pre-incubated at 37° C. and substrate (50 μM) is added after 5 minutes. The absorbance change at 400 nm is monitored for 20 minutes. This substrate has previously been reported as a substrate for classical calcium-dependent $PLA_2$s. (Washburn, W. N. and Dennis, E. A., J.Amer Chem.Soc., 1990, 112,2040–2041); or (b) Protein Content Total protein content (i.e. enzyme content) can be determined using polyclonal antiserum raised against purified human $Lp-PLA_2$. The antisera recognises both native and glycosylated enzyme as measured by immunoprecipitation of activity and Western Blot analysis.

Polyclonal antiserum was prepared as follows. Immunisation of rabbits involved mixing 0.5 ml of purified human $Lp-PLA_2$ (=100 μg) with an equal volume of Freund's complete adjuvant. The final emulsion was given subcutaneously in 4×0.25 ml injections. Boosting using a Freund's incomplete adjuvant\antigen mixture (4×0.25 ml subcut; dosage=50 μg) took place 4 weeks later. Adequate titre was evident at between 6–8 weeks from initial injection.

Figure 1:
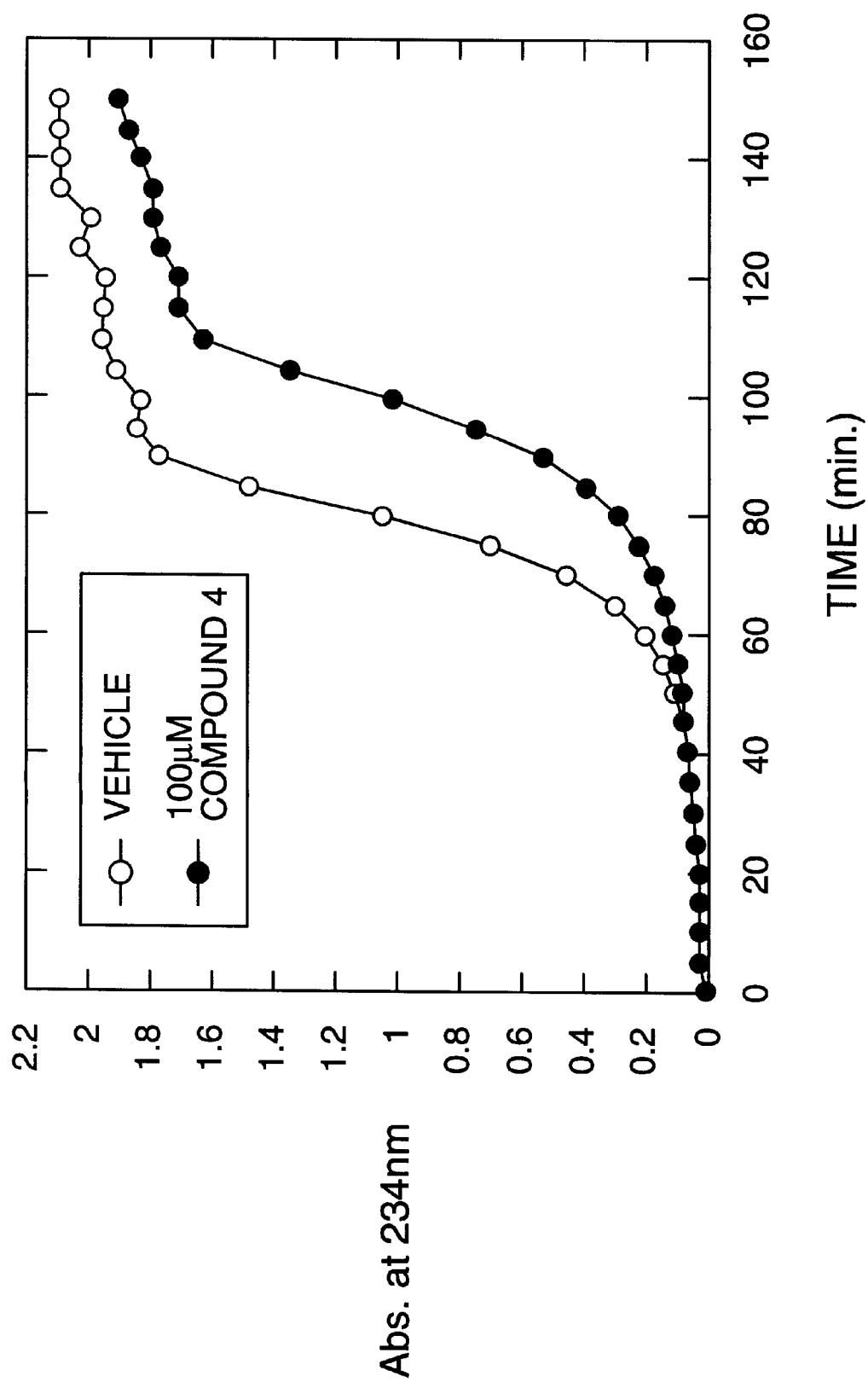
FIG. 1 is a graph of absorbance at 234 nm against time (min) in a study of inhibition of copper (5 μM)—stimulated LDL (150 μg/ml) oxidation by compound 4 vs control vehicle.
Figure 2:
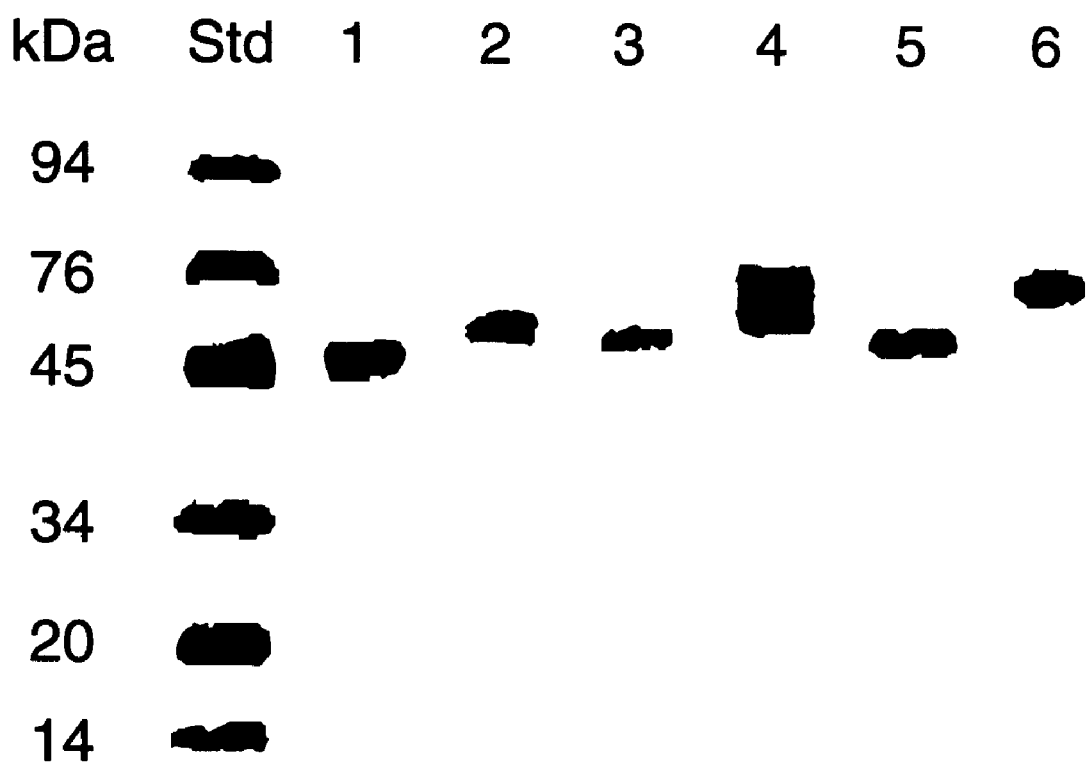
FIG. 2 is an analysis the purified $Lp-PLA_2$ material of Example 4 following separation by polyacrylamide gel electrophoresis. Lanes 2, 4 and 6 contain adjacent fractions of purified native $Lp-PLA_2$. Lanes 1, 3 and 5 are fractions 2, 4 and 6 respectively after N-deglycosylation.

We claim:

1. An enzyme fragment selected from the group consisting of SEQ ID NOs:1, 2, 4, 10 and 11.

2. An enzyme lipoprotein associated phospholipase $A_2$ comprising the amino acid sequence of SEQ ID NO:9, which is at least 95% pure relative to other protein contaminants.

3. An enzyme lipoprotein associated phospholipase $A_2$ consisting of the amino acid sequence of SEQ ID NO:9, which is at least 95% pure relative to other protein contaminants.

4. An enzyme lipoprotein associated phospholipase $A_2$ comprising the amino acid sequence encoded by nucleic acids 1139 to 1249 of SEQ ID NO:9, which is at least 95% pure reltive to other protein contaminants.

5. The enzyme lipoprotein associated phospholipase $A_2$ comprising the amino acid sequence corresponding to amino acid residues 231 to 441 of SEQ ID NO:9, which is at least 95% pure relative to other protein contaminants.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
       (A) LENGTH: 37 amino acids
       (B) TYPE: amino acid
       (C) STRANDEDNESS:
       (D) TOPOLOGY: linear (ii) MOLECULE TYPE: peptide (iii) HYPOTHETICAL: NO (iv) FRAGMENT TYPE:

(v) FRAGMENT TYPE: internal (vi) ORIGINAL SOURCE:

(x) FEATURE:

(xi) SEQUENCE DESCRIPTION: SEQ ID NO: 1:

Met Leu Lys Leu Lys Gly Asp Ile Asp Ser Asn Ala Ala Ile Asp Leu
1               5                   10                  15

Ser Asn Lys Ala Ser Leu Ala Phe Leu Gln Lys His Leu Gly Leu His
                20                  25                  30

Lys Asp Phe Asp Gln
            35

(2) INFORMATION FOR SEQ ID NO: 2:

(i) SEQUENCE CHARACTERISTICS:
       (A) LENGTH: 30 amino acids
       (B) TYPE: amino acid
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 2:

Trp Met Phe Pro Leu Gly Asp Glu Val Tyr Ser Arg Ile Pro Gln Pro
1               5                   10                  15

Leu Phe Phe Ile Asn Ser Glu Tyr Phe Gln Tyr Pro Ala Asn
                20                  25                  30

(2) INFORMATION FOR SEQ ID NO: 3:

(i) SEQUENCE CHARACTERISTICS:
       (A) LENGTH: 27 amino acids
       (B) TYPE: amino acid
       (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 3:

Gln Tyr Ile Asn Pro Ala Val Met Ile Thr Ile Arg Gly Ser Val His
1               5                   10                  15

```
Gln Asn Phe Ala Asp Phe Thr Phe Ala Thr Gly
         20                  25
```

(2) INFORMATION FOR SEQ ID NO: 4:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 4:

```
Trp Leu Met Gly Asn Ile Leu Arg Leu Leu Phe Gly Ser Met Thr Thr
1               5                   10                  15

Pro Ala Asn
```

(2) INFORMATION FOR SEQ ID NO: 5:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 5:

```
AAAAAACCTA TTTTAATCCT AATTGTATTT CTCTATTCCT GAAGAGTTCT GTAACATGAT    60

GTGTTGATTG GTTGTGTTAA TGTTGGTCCC TGGAATAAGA TTCTCATCAT CTCCTTCAAT   120

CAAGCAGTCC CACTGATCAA ATCTTTATG AAGTCCTAAA TGCTTTTGTA AGAATGCTAA    180

TGAAGCTTTG TTGCTAAGAT CAATAGCTGC ATTTGAATCT ATGTCTCCCT TTAATTTGAG   240

CATGTGTCCA ATTATTTTGC CAGTNGCAAA AGTGAAGTCA GCAAAATTCT GGTGGACTGA   300

ACCCCTGATT GTAATCATCT TTCTTTCTTT ATCAGGTGAG TAGCATTTTT TCATTTTTAT   360

GATATTAGCA GGATATTGGA AATATTCAGN GTTGNTAAAA AGNGGNGGCT GAGGGATTCT   420
```

(2) INFORMATION FOR SEQ ID NO: 6:

(i) SEQUENCE CHARACTERISTICS:
        (A) LENGTH: 379 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 6:

```
TGCTAATATC ATAAAAATGA AAAAATGCTA CTCACCTGAT AAAGAAAGAA AGATGATTAC    60

AATCAGGGGT TCAGTCCACC AGANTTTTGC TGACTTCACT TTTGCAACTG GCAAAATAAT   120

TGGACACATG CTCAAATTAA AGGGAGACAT AGATTCAAAT GTAGCTATTG ATCTTAGCAA   180

CAAAGCTTCA TTAGCATTCT TACAAAAGCA TTTAGGACTT CATAAAGATT TGTTCAGTG    240
```

```
GGACTGCTTG ATTGAAGGAG ATGATGAGAA TCTTATTCCA GGGACCAACA TTAACACAAC      300

CAATTCAACA CATCATGTTT ACAGAACTTC TTCCAGGGAA TAGGAGGAAA TACAATTGGG      360

GTTTAAAATA GGTTTTTTT                                                   379
```

(2) INFORMATION FOR SEQ ID NO: 7:

(i) SEQUENCE CHARACTERISTICS:
        (A) LENGTH: 279 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 7:

```
GAAGAATGCA TTAGATTTAA AGTTTGATAT GGAACAACTG AAGGACTCTA TTGATAGGGA       60

AAAAATAGCA GTAATTGGAC ATTCTTTTGG TGGAGCAACG GTTATTCAGA CTCTTAGTGA      120

AGATCAGAGA TTCAGATGTG GTATTGCCCT GGATGCATGG ATGTTTCCAC TGGGTGATGA      180

AGTATATTCC AGAATTCCTC AGCCCCTCTT TTTTATCAAC TCTGAATATT TCCAATATCC      240

TGCTAATATC ATAAAANTGG AAAAATGCTA CTCACCTGG                             279
```

(2) INFORMATION FOR SEQ ID NO: 8:

(i) SEQUENCE CHARACTERISTICS:
        (A) LENGTH: 572 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 8:

```
AAAATAGCAG TAATTGGACA TTCTTTAGGT GGAGCAACGG TTATTCAGAC TCTTAGTGAA       60

GATCAGAGAT TCAGATGTGG TATTGCCCTG GATGCATGGA TGTTTCCACT GGGTGATGAA      120

GTATATTCCA GAATTCCTCA GCCCCTCTTT TTTATCAACT CTGAATATTT CCAATATCCT      180

GCTAATATCA TAAAAATGAA AAAATGCTAC TCACCTGATA AGAAAGAAA GATGATTACA       240

ATCAGGGGTT CAGTCCACCA GAATTTTGCT GACTTCACTT TTGCAACTGG CAAAATAATT      300

GGACACATGC TCAAATTAAA GGGAGACATA GATTCAAATG TAGCTATTGA TCTTAGCAAC      360

AAAGCTTCAT CAGCATTCTT ACAAAAGCAT TTAGGACTTC ATAAAGATTT TGATCAGTGG      420

GACTGCTTGA TTGAAGGAGA TGATGAGAAT CTTATTCCAG GGACCAACAT TAACACAACC      480

AATCAACACA TCATGTTACA GAACTCTTCA GGAATAGAGA AATACAATTA GGATTAAAAT      540

AGGTTTTTTA AAAAAAAAA AAAAAAACT CG                                     572
```

(2) INFORMATION FOR SEQ ID NO: 9:

(i) SEQUENCE CHARACTERISTICS:
        (A) LENGTH: 1361 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (ix) FEATURE:
    (A) NAME/KEY: CDS
    (B) LOCATION: 38..1360

(xi) SEQUENCE DESCRIPTION: SEQ ID NO: 9:

```
TGAGAGACTA AGCTGAAACT GCTGCTCAGC TCCCAAG ATG GTG CCA CCC AAA TTG        55
                                        Met Val Pro Pro Lys Leu
                                         1               5

CAT GTG CTT TTC TGC CTC TGC GGC TGC CTG GCT GTG GTT TAT CCT TTT        103
His Val Leu Phe Cys Leu Cys Gly Cys Leu Ala Val Val Tyr Pro Phe
                10                  15                  20

GAC TGG CAA TAC ATA AAT CCT GTT GCC CAT ATG AAA TCA TCA GCA TGG        151
Asp Trp Gln Tyr Ile Asn Pro Val Ala His Met Lys Ser Ser Ala Trp
            25                  30                  35

GTC AAC AAA ATA CAA GTA CTG ATG GCT GCT GCA AGC TTT GGC CAA ACT        199
Val Asn Lys Ile Gln Val Leu Met Ala Ala Ala Ser Phe Gly Gln Thr
        40                  45                  50

AAA ATC CCC CGG GGA AAT GGG CCT TAT TCC GTT GGT TGT ACA GAC TTA        247
Lys Ile Pro Arg Gly Asn Gly Pro Tyr Ser Val Gly Cys Thr Asp Leu
55                  60                  65                  70

ATG TTT GAT CAC ACT AAT AAG GGC ACC TTC TTG CGT TTA TAT TAT CCA        295
Met Phe Asp His Thr Asn Lys Gly Thr Phe Leu Arg Leu Tyr Tyr Pro
                75                  80                  85

TCC CAA GAT AAT GAT CGC CTT GAC ACC CTT TGG ATC CCA AAT AAA GAA        343
Ser Gln Asp Asn Asp Arg Leu Asp Thr Leu Trp Ile Pro Asn Lys Glu
            90                  95                 100

TAT TTT TGG GGT CTT AGC AAA TTT CTT GGA ACA CAC TGG CTT ATG GGC        391
Tyr Phe Trp Gly Leu Ser Lys Phe Leu Gly Thr His Trp Leu Met Gly
        105                 110                 115

AAC ATT TTG AGG TTA CTC TTT GGT TCA ATG ACA ACT CCT GCA AAC TGG        439
Asn Ile Leu Arg Leu Leu Phe Gly Ser Met Thr Thr Pro Ala Asn Trp
    120                 125                 130

AAT TCC CCT CTG AGG CCT GGT GAA AAA TAT CCA CTT GTT GTT TTT TCT        487
Asn Ser Pro Leu Arg Pro Gly Glu Lys Tyr Pro Leu Val Val Phe Ser
135                 140                 145                 150

CAT GGT CTT GGG GCA TTC AGG ACA CTT TAT TCT GCT ATT GGC ATT GAC        535
His Gly Leu Gly Ala Phe Arg Thr Leu Tyr Ser Ala Ile Gly Ile Asp
                155                 160                 165

CTG GCA TCT CAT GGG TTT ATA GTT GCT GCT GTA GAA CAC AGA GAT AGA        583
Leu Ala Ser His Gly Phe Ile Val Ala Ala Val Glu His Arg Asp Arg
            170                 175                 180

TCT GCA TCT GCA ACT TAC TAT TTC AAG GAC CAA TCT GCT GCA GAA ATA        631
Ser Ala Ser Ala Thr Tyr Tyr Phe Lys Asp Gln Ser Ala Ala Glu Ile
        185                 190                 195

GGG GAC AAG TCT TGG CTC TAC CTT AGA ACC CTG AAA CAA GAG GAG GAG        679
Gly Asp Lys Ser Trp Leu Tyr Leu Arg Thr Leu Lys Gln Glu Glu Glu
    200                 205                 210

ACA CAT ATA CGA AAT GAG CAG GTA CGG CAA AGA GCA AAA GAA TGT TCC        727
Thr His Ile Arg Asn Glu Gln Val Arg Gln Arg Ala Lys Glu Cys Ser
215                 220                 225                 230

CAA GCT CTC AGT CTG ATT CTT GAC ATT GAT CAT GGA AAG CCA GTG AAG        775
Gln Ala Leu Ser Leu Ile Leu Asp Ile Asp His Gly Lys Pro Val Lys
                235                 240                 245

AAT GCA TTA GAT TTA AAG TTT GAT ATG GAA CAA CTG AAG GAC TCT ATT        823
Asn Ala Leu Asp Leu Lys Phe Asp Met Glu Gln Leu Lys Asp Ser Ile
            250                 255                 260

GAT AGG GAA AAA ATA GCA GTA ATT GGA CAT TCT TTT GGT GGA GCA ACG        871
```

```
Asp Arg Glu Lys Ile Ala Val Ile Gly His Ser Phe Gly Gly Ala Thr
        265                 270                 275

GTT ATT CAG ACT CTT AGT GAA GAT CAG AGA TTC AGA TGT GGT ATT GCC      919
Val Ile Gln Thr Leu Ser Glu Asp Gln Arg Phe Arg Cys Gly Ile Ala
280                     285                 290

CTG GAT GCA TGG ATG TTT CCA CTG GGT GAT GAA GTA TAT TCC AGA ATT      967
Leu Asp Ala Trp Met Phe Pro Leu Gly Asp Glu Val Tyr Ser Arg Ile
295                 300                 305                 310

CCT CAG CCC CTC TTT TTT ATC AAC TCT GAA TAT TTC CAA TAT CCT GCT     1015
Pro Gln Pro Leu Phe Phe Ile Asn Ser Glu Tyr Phe Gln Tyr Pro Ala
                315                 320                 325

AAT ATC ATA AAA ATG AAA AAA TGC TAC TCA CCT GAT AAA GAA AGA AAG     1063
Asn Ile Ile Lys Met Lys Lys Cys Tyr Ser Pro Asp Lys Glu Arg Lys
            330                 335                 340

ATG ATT ACA ATC AGG GGT TCA GTC CAC CAG AAT TTT GCT GAC TTC ACT     1111
Met Ile Thr Ile Arg Gly Ser Val His Gln Asn Phe Ala Asp Phe Thr
        345                 350                 355

TTT GCA ACT GGC AAA ATA ATT GGA CAC ATG CTC AAA TTA AAG GGA GAC     1159
Phe Ala Thr Gly Lys Ile Ile Gly His Met Leu Lys Leu Lys Gly Asp
360                 365                 370

ATA GAT TCA AAT GCA GCT ATT GAT CTT AGC AAC AAA GCT TCA TTA GCA     1207
Ile Asp Ser Asn Ala Ala Ile Asp Leu Ser Asn Lys Ala Ser Leu Ala
375                 380                 385                 390

TTC TTA CAA AAG CAT TTA GGA CTT CAT AAA GAT TTT GAT CAG TGG GAC     1255
Phe Leu Gln Lys His Leu Gly Leu His Lys Asp Phe Asp Gln Trp Asp
                395                 400                 405

TGC TTG ATT GAA GGA GAT GAT GAG AAT CTT ATT CCA GGG ACC AAC ATT     1303
Cys Leu Ile Glu Gly Asp Asp Glu Asn Leu Ile Pro Gly Thr Asn Ile
            410                 415                 420

AAC ACA ACC AAT CAA CAC ATC ATG TTA CAG AAC TCT TCA GGA ATA GAG     1351
Asn Thr Thr Asn Gln His Ile Met Leu Gln Asn Ser Ser Gly Ile Glu
        425                 430                 435

AAA TAC AAT T                                                        1361
Lys Tyr Asn
    440
```

(2) INFORMATION FOR SEQ ID NO: 10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 10:

```
Gln Tyr Ile Asn Pro Val Ala
1               5
```

(2) INFORMATION FOR SEQ ID NO: 11:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 11:

Met Ile Thr Ile Arg Gly Ser Val His Gln Asn Phe Ala Asp Phe Thr
1               5                   10                  15

Phe Ala Thr Gly
            20